US005450144A

United States Patent [19]
Ben Nun

[11] Patent Number: 5,450,144
[45] Date of Patent: Sep. 12, 1995

[54] OPHTHALMOLOGIC EXAMINATION AND/OR TREATMENT APPARATUS INCLUDING ILLUMINATOR AND MAGNIFIYER ASSEMBLY

[75] Inventor: Joshua Ben Nun, Doar Vitkin, Israel

[73] Assignee: Optiko Scientific Ltd., Tel-Aviv, Israel

[21] Appl. No.: 118,844

[22] Filed: Sep. 10, 1993

[30] Foreign Application Priority Data

Sep. 25, 1992 [IL]  Israel ..................... 103290

[51] Int. Cl.⁶ .................. A61B 3/10; A61B 3/125; A61B 1/06
[52] U.S. Cl. .................. 351/219; 351/205; 351/220; 351/221; 600/168
[58] Field of Search ............. 351/219, 220, 221, 206, 351/208, 212, 246, 247, 200, 205; 128/745, 4, 6; 606/4, 5, 6

[56] References Cited

U.S. PATENT DOCUMENTS

| | | | |
|---|---|---|---|
| 3,871,772 | 3/1975 | Munnerlyn et al. | 356/153 |
| 3,944,341 | 3/1976 | Pomerantzeff | 351/206 |
| 4,056,310 | 11/1977 | Shimizu et al. | 351/219 |
| 4,251,139 | 2/1981 | Matsumura | 351/206 |
| 4,978,213 | 12/1990 | El Hage | 351/212 |
| 5,072,731 | 12/1991 | Taratuta et al. | 128/745 X |
| 5,116,114 | 5/1992 | Nakamura et al. | 606/4 X |

FOREIGN PATENT DOCUMENTS

| | | |
|---|---|---|
| 0109846 | 5/1984 | European Pat. Off. . |
| 0554643 | 8/1993 | European Pat. Off. . |
| 3124305 | 1/1983 | Germany . |
| 2034916 | 6/1980 | United Kingdom . |

*Primary Examiner*—William L. Sikes
*Assistant Examiner*—David R. Parsons
*Attorney, Agent, or Firm*—Benjamin J. Barish

[57] ABSTRACT

Ophthalmologic apparatus includes a light source for obliquely directing light beams into an eye to be examined to illuminate a region of interest therein, a lens system for viewing the region of interest, an optical magnifier assembly for magnifying the viewed region of interest, and an image intensifier for intensifying the image of the viewed region of interest. The light source directs light into the eye from opposite sides thereof to intersect in the plane of the region of interest in the eye.

14 Claims, 6 Drawing Sheets

OPHTHALMOLOGIC EXAMINATION AND/OR TREATMENT APPARATUS INCLUDING ILLUMINATOR AND MAGNIFIYER ASSEMBLY

FIELD AND BACKGROUND OF THE INVENTION

The present invention relates to ophthalmologic apparatus particularly useful for eye examination and/or for treatment of various eye disorders.

Studies show that some of the leading causes of blindness are accompanied by pathologic development of the vascular net in the retina. One of these pathologies is a vascular net in the chorio-retinal complex. This net is supplied by only a few feeding vessels. Generally speaking, the presently-available ophthalmologic apparatus is capable of only regional examination and regional treatment, and is incapable of examination and/or treatment at the capillary level. As a result, the use of such apparatus does not enable detailed examination of the capillary blood vessels in the pathologic vascular net nor accurate location of the few vessels feeding the pathologic vascular net. These limitations limit the usefulness of the known apparatus for eye examination and/or treatment.

OBJECTS AND BRIEF SUMMARY OF THE INVENTION

An object of the present invention is to provide ophthalmologic apparatus having advantages in the above respects, particularly in enabling an accurate examination and/or treatment of the vascular net at the capillary (retinal and choroidal) level.

According to the present invention, there is provided ophthalmologic apparatus comprising: illuminating means for directing light into an eye to be examined to illuminate a region of interest therein; a lens system for viewing the region of interest of the eye to be examined; an optical magnifier assembly for magnifying the viewed region of interest; and an image intensifier for intensifying the image of the viewed region of interest.

According to one feature of the present invention, the illuminating means comprises an annular light source; and an annular reflector coaxial with the annular light source for reflecting the light into the eye from all sides thereof to intersect in the plane of the region of interest in the eye.

According to another aspect of the present invention, the apparatus further includes an endoscope adapted to penetrate the eye for viewing a selected region thereof.

Such an apparatus is useful when a fluorescent material is injected into the patient to enable viewing the blood flow in the eye. The provision of the image intensifier (which may be a known light amplifier) minimizes the intensity of the light required for illumination, thereby producing less light toxicity and less interference from scattered light. It also minimizes the amount of fluorescent material required to be injected, thereby not only saving on the cost of such material, but also minimizing leakage of the material to surrounding tissue and background noise, thereby producing better resolution.

Apparatus constructed in accordance with the foregoing features enables the apparatus to view under magnification blood vessels at the capillary level and thereby to assess the condition of the eye, as well as other health conditions of the subject which may be indicated by the condition of the eye. The apparatus may also be used for treatment of the eye, at the capillary level, by means of a laser beam.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
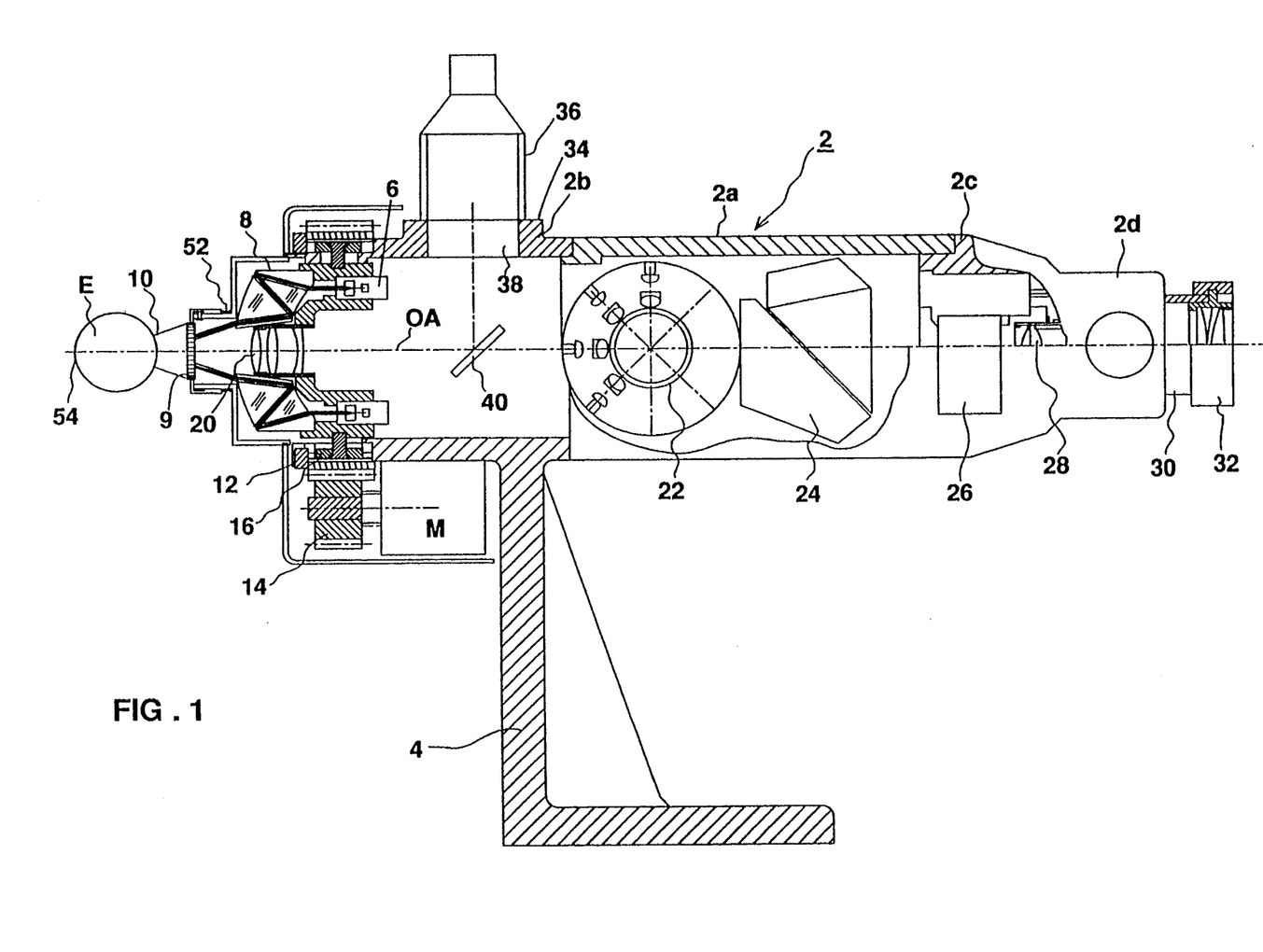
FIG. 1 is a side elevational view, partly in section, illustrating one form of non-invasive ophthalmologic examination apparatus constructed in accordance with the present invention.
Figure 2:
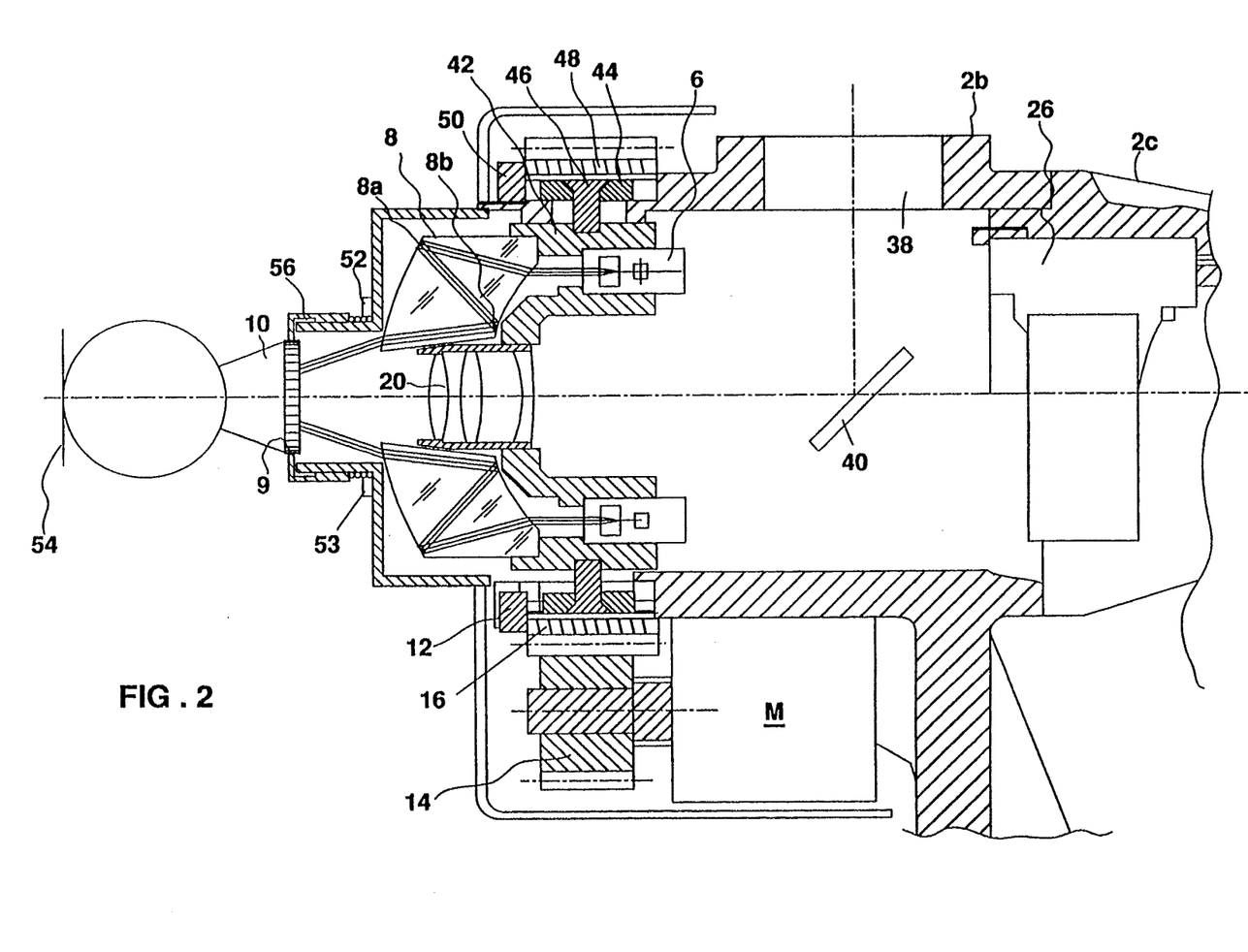
FIG. 2 is an enlarged view of a portion of FIG. 1.

The apparatus illustrated in FIGS. 1 and 2 is a non-invasive type of apparatus for examining the eye with respect to various types of eye disorders, and also for treating the eye if necessary by means of a laser beam. The apparatus includes a housing, generally designated 2, comprising a main section 2a, a front section 2b, and two rear sections 2c and 2d. The housing 2 is mounted to any suitable support by a bracket 4 integrally formed with the front housing section 2b.

The front housing section 2b includes an annular light source 6 coaxial with the optical axis OA of the apparatus and adapted to illuminate the eye (shown at E) to be examined or treated by the use of the apparatus. The annular light source 6 is in the form of a circular array of point light emitters, or LEDs (light emitting diodes), projecting light beams forwardly of the apparatus and parallel to its optical axis OA. The annular array of light beams are reflected by an annular lens 8 out through an opening 9 in the front end of the housing covered by a contact lens 10 which is brought into direct contact with the eye E being examined or treated. Annular lens 8 is a catadioptric or mirror lens having a first annular reflector surface 8a (FIG. 2) on its forward side and a second annular reflector surface 8b on its rear side for reflecting the light through the housing opening 9 obliquely to the optical axis OA and to the eye E being examined via the contact lens 10.

It will thus be seen that in the arrangement illustrated in FIGS. 1 and 2, the light enters the eye from a plurality of sides of the eye obliquely to the optical axis OA of the apparatus and of the eye. The oblique angle of the light entering the eye is selected so that the light from a plurality of sources intersects in the plane of the region of interest in the eye, to thereby provide intense illumination of that region of interest. To permit preselecting the plane of intersection of the light beams, the annular lens 8 and contact lens 10 are mounted on a head 12 which is movable axially of the apparatus, towards or away from the eye, by a motor M. Motor M is carried by the head 12 and drives a pinion 14 which meshes with a gear hub 16 carried by the forward housing section 2b. The arrangement is such that rotation of pinion 14 moves head 12, and with it the annular lens 8 and contact lens 10 towards or away from the eye.

The light reflected from the interior of the eye E passes through the contact lens 10, through a lens system 20 also carried by the front housing section 2b, and then through the main housing section 2a and the two rear housing sections 2c, 2d. The main housing section 2a includes a magnifier assembly, generally designated 22, in the form of a rotatable turret which may be rotated in order to select a desired magnification. The main housing section 2a further includes a beam-folding prism 24 for reducing the total length of the housing in order to focus the light emitted from the eye E at the rear end of the housing, i.e., at the end of the rear housing section 2d.

Figure 9:
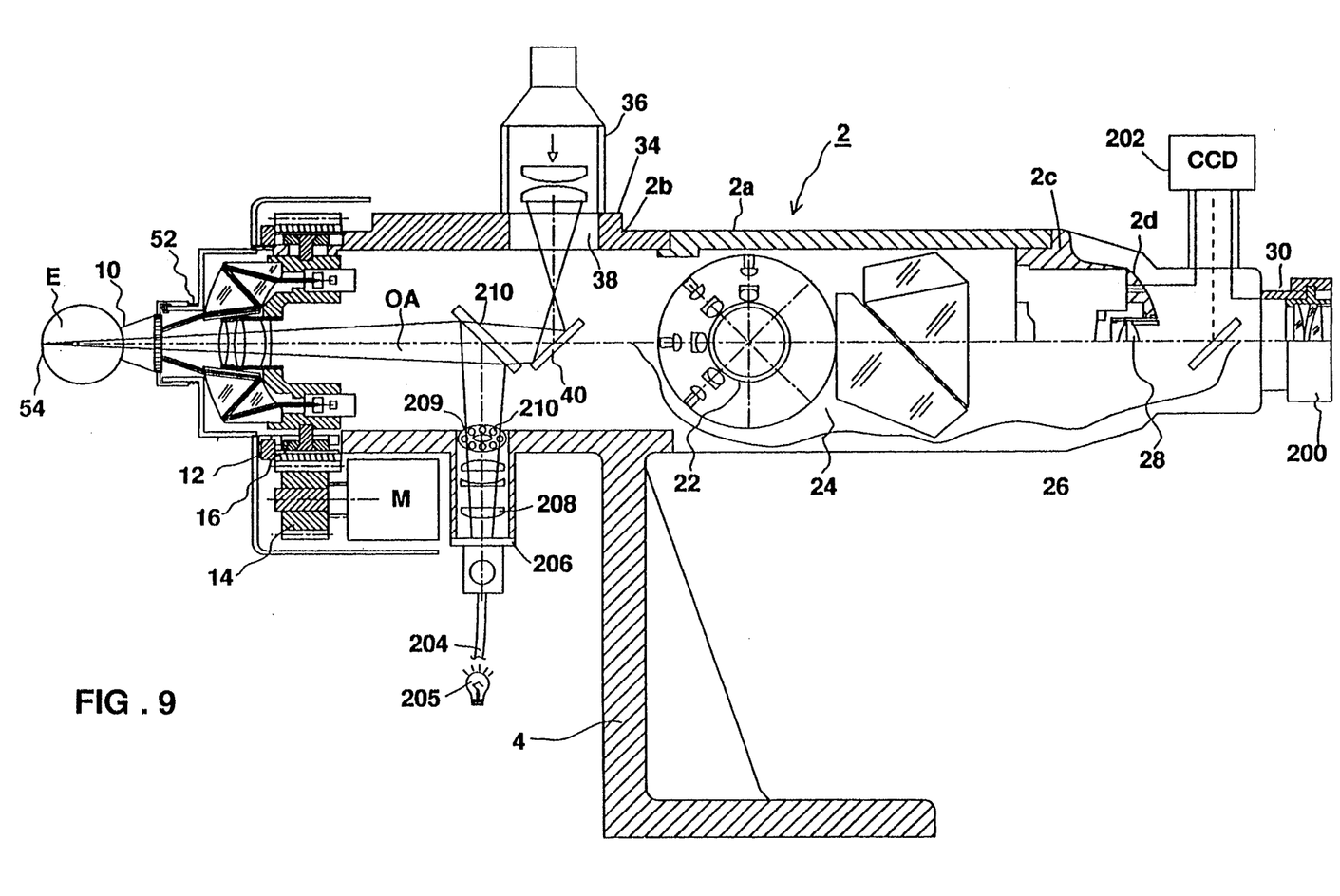
FIG. 9 is a fragmentary view illustrating the apparatus including an attachment to a video camera for also recording or remotely viewing the interior of the eye.

Housing section 2c houses an image intensifier 26 which intensifies the image of the eye. The rearmost housing section 2d houses a lens system 28 for focussing the light, and also a coupling collar 30 at the end of the housing section for attaching an eyepiece 32 to enable eye viewing the image. Coupling 30 may also be used for attaching thereto a video camera (as shown in FIG. 9), e.g., a CCD array, for displacing the eye image at another location, and/or for recording it.

The front housing 2b further includes a connector 34 for attaching thereto a laser 36 adapted to project a laser beam into the eye E, e.g., for treating the eye. The laser attachment 34 aligns the laser 36 with an opening 38 in the front housing section 2b substantially perpendicular to the optical axis OA. A beam splitter 40 reflects the laser beam out through the front housing opening 9 into the eye E via the contact lens 10. Beam splitter 40 also transmits therethrough the light reflected from the viewed region of the eye entering the housing via contact lens 10 to the opposite end of the housing occupied by eyepiece 32.

Annular lens 8 also serves as a zoom lens to enable the size of the viewed region of interests of the eye to be rapidly changed. For this purpose the mirror lens 8 is mounted on a lens collar 42. Collar 42 is fixed to a zoom sleeve 44 (FIG. 2) by a pin 46 and meshes with the hub of a gear 48 which may be manually rotated driving a pinion 50 meshing with gear 48. Annular lens 8 may thus be moved in the axial direction, parallel to the optical axis OA, with respect to its annular light source 6.

Contact lens 10 is floatingly mounted by a coiled spring assembly 52 to the front end of the front housing section 2b so that it may be brought into direct contact with the eye E being examined, without applying undue pressure to the eye. A pressure control unit 53 (FIG. 2) cooperable with spring assembly 52 provides accurate measurement of the pressure applied on the eye, and can be used for either controlling motor M and/or an indicator (not shown) to prevent excessive pressure from being applied to the eye, and/or for providing an indication if excessive pressure Should be applied to the eye.

The distance between the contact lens 10 to the relay system 20 may be adjusted by means of a threaded fastener 56 (FIG. 2) to compensate for variations in the RPE (retinal pigment epithelium) location 54 which varies with the eye size.

The manner of using the apparatus illustrated in FIGS. 1 and 2 will be apparent from the above description. Thus, the apparatus is positioned to bring the contact lens 10 into direct contact with the subject's eye E, while the coiled spring 52 carrying the contact lens, and the pressure sensor 53, prevent undue pressure on the eye. Compensation for variations in the location of the RPE 54 because of the eye size may be made by the use of threaded fastener 56.

The interior of the eye is illuminated by the annular series of light sources 6 projecting the light through the annular lens 8 within the housing 2 into the eye E via the contact lens 10. As described earlier, the light entering the eye obliquely from many sides is preset to intersect in the plane of the region of interest in the eye. Such an arrangement provides relative intense illumination at the region of interest, and at the same time minimizes interference with the light reflected from the eye and to be observed during the examination.

The light reflected from the eye E is passed through the relay lens 20 and the magnifier assembly 22, the beam folding prism 24, the image intensifier 26 and the lens system 28, and may be viewed through the eyepiece 32 (or a video camera) at the opposite end of the apparatus. Magnifier assembly turret 22 may be rotated to select any desired magnification, e.g., from 20× to about 250×. If the size of the viewed region of interest of the eye is to be changed, gear 48 may be manually rotated to move the lens collar 42 of the annular mirror lens 8 forwardly or rearwardly with respect to the contact lens 10.

If the eye is also to be treated by a laser beam, laser 36 is attached via the attachment 34 to project its laser beam through opening 38 into the interior of the housing. Beam splitter 40 reflects the laser beam along the optical axis OA into the subject's eye E via the contact lens 10. The light emitted from the eye E passes through the relay lens 20, beam splitter 40, magnifier assembly 22, beam folding prism 24, image intensifier 26, and eyepiece 32 at the opposite end of the apparatus. If it is desired to transmit the image of the eye to another location or to record it, this can be done by replacing the eyepiece 32 with a video camera unit, such as a CCD a shown in FIG. 9.

Figure 3:
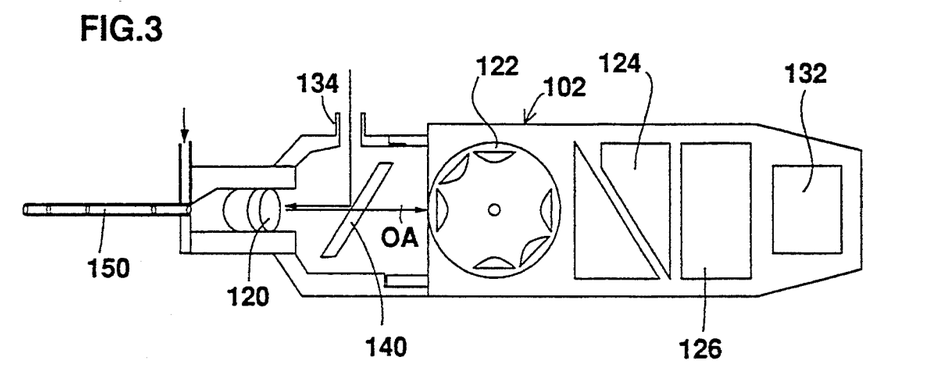
FIG. 3 is a side elevational view illustrating an invasive type of ophthalmologic examination apparatus constructed in accordance with the present invention.

FIG. 3 illustrates an implementation of the invention in another type of ophthalmologic apparatus for examining and/or treating an eye disorder. The apparatus illustrated in FIG. 3 includes a housing 102, of similar construction as in FIGS. 1 and 2, enclosing a turret-type magnifier assembly 122, a beam folding prism 124, and an image intensifier 126. Housing 102 in FIG. 3 also includes an attachment 134 for attaching a laser to project a laser beam to a beam splitter 140 which reflects the laser beam along the optical axis OA of the apparatus into the eye being examined, and passes the image reflected from the eye through the relay lens assembly 120, magnifier assembly 122, beam folding prism 124, and image intensifier 126 to the eyepiece 132 at the opposite end of the apparatus.

Figure 4:
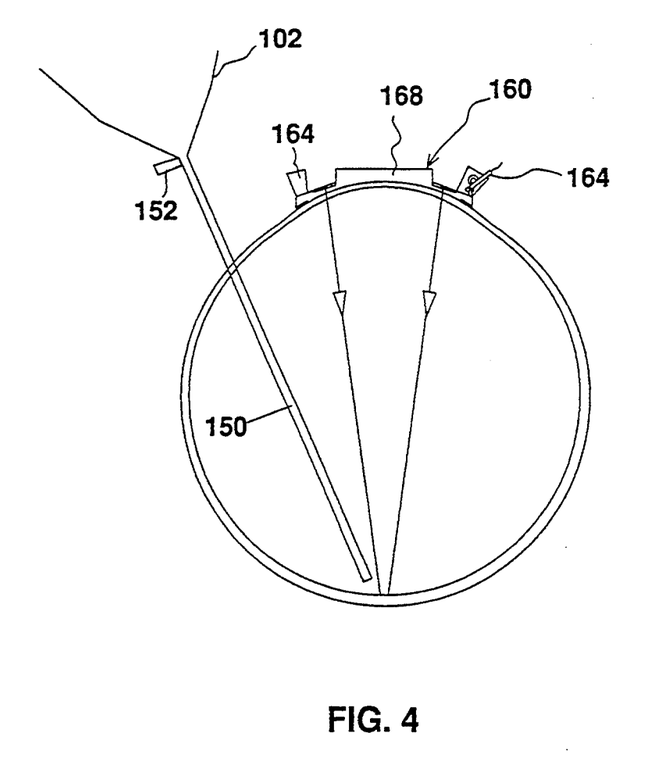
FIG. 4 diagrammatically illustrates the manner of using the invasive-type of apparatus of FIG. 3 for examination and/or treatment of an eye disorder.

However, the apparatus of FIG. 3 does not include a contact lens, corresponding to contact lens 10 at the front part of the apparatus for contact with the eye being examined; rather, it includes an endoscope 150 adapted to penetrate the eye, as shown in FIG. 4. As further shown in FIG. 4, the interior of the eye is illuminated by a separate illuminator, generally designated 160, which is placed into contact with the eye, and not by an illuminator within the housing 102, as in the FIGS. 1 and 2 apparatus.

The endoscope 150 may contain an irrigation/aspiration port 152, and fiber optics for illumination. In that case, the illuminator 160 is not needed. Since the space in the endoscope is limited, using part of it for illuminating fibers would be on the account of the image quality achieved by the system.

Illuminator 160, for illuminating the eye being examined and/or treated, is illustrated in FIGS. 4–7. This illuminator is also of annular shape. It includes an annular-shaped lens 162, and an annular array of light sources 164 supported around the outer periphery of the annular lens 162 and oriented such that the lens reflects the lens from the light sources into the eye. For this purpose, the annular lens 162 includes an annular reflector surface 162a (FIG. 7) on the front face of the lens in contact with the eye, and an annular reflector surface 162b on its rear face, such that the light is directed by the two reflector surfaces inwardly of the eye along an annular array of converging paths as illustrated by arrows 166 in FIGS. 5 and 7, while the eye is observed via the window 168 in the illuminator as indicated by arrow 169 in FIG. 7.

As shown particularly in FIG. 4, the light enters the eye obliquely from a plurality of sides and intersects at the plane of the region of interest in the eye. As described above with respect to the FIGS. 1 and 2 embodiment, such an illumination system maximizes the intensity of illumination of the region of interest and also minimizes the interference with the light reflected back out of the eye to enable viewing the region of interest.

Figure 7:
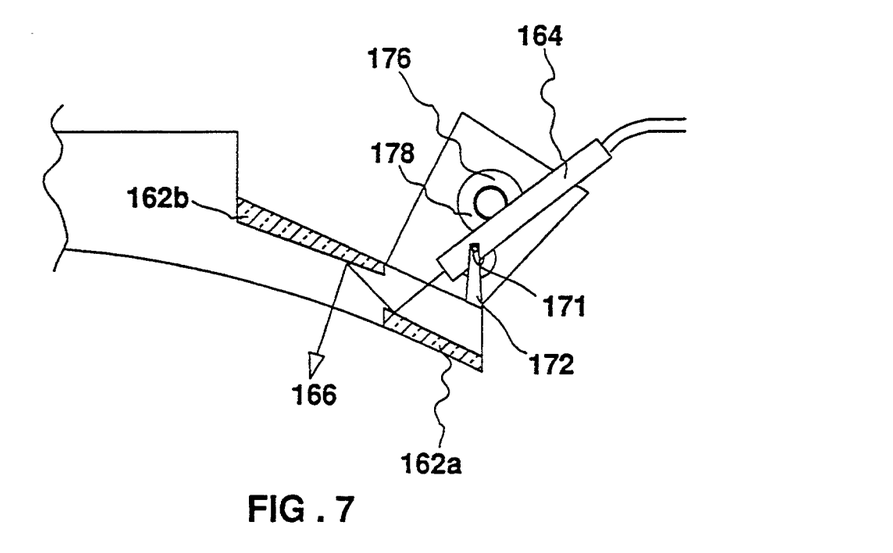
FIG. 7 is an enlarged fragmentary view illustrating the mounting of one of the light sources in the annular illumnator of FIGS. 5 and 6.

The annular array of light sources 164 may be point light emitters, such as LEDs, optical fibers, or the like. Each light source 164 is pivotally mounted by a pin 171 to a pair of posts 172 formed on a ring 174 extending around the periphery of the annular lens 162, to vary the angle of the light sources with respect to the optical axis of the illuminator, and of the eye, in order to change the plane of the point of intersection of their light beams within the eye. For this purpose, each light source 164 is formed with an ear 176 at its upper end adapted to receive a common adjusting ring 178 of variable diameter, such that increasing the diameter of adjusting ring 178 pivots all the light sources 164 simultaneously in one direction, and decreasing the diameter of ring 170 pivots the light sources simultaneously in the opposite direction.

Figure 8:
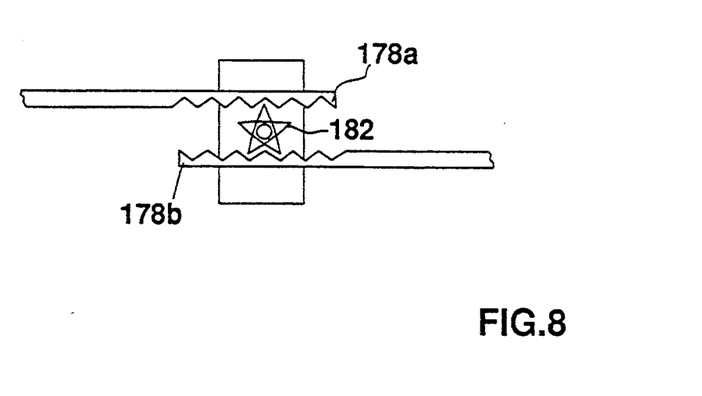
FIG. 8 is a fragmentary view illustrating the manner of simultaneously adjusting all the light sources in the annular illuminator of FIGS. 5-7.

Annular illuminator 160 is provided with a knob 180 (FIG. 5) which may be manually rotated in order to increase or decrease the diameter of adjusting ring 178. This is more particularly illustrated in FIGS. 5 and 8, wherein it will be seen that the two ends of adjusting ring 178 are formed with teeth, as shown at 178a, 178b, engageable with a toothed wheel 182 fixed to knob 180, such that rotation of the knob in one direction draws the ends 178a, 178b of the adjusting ring together to decrease its diameter, whereas rotating the knob in the opposite direction moves the two ends apart to increase the diameter.

Figure 5:
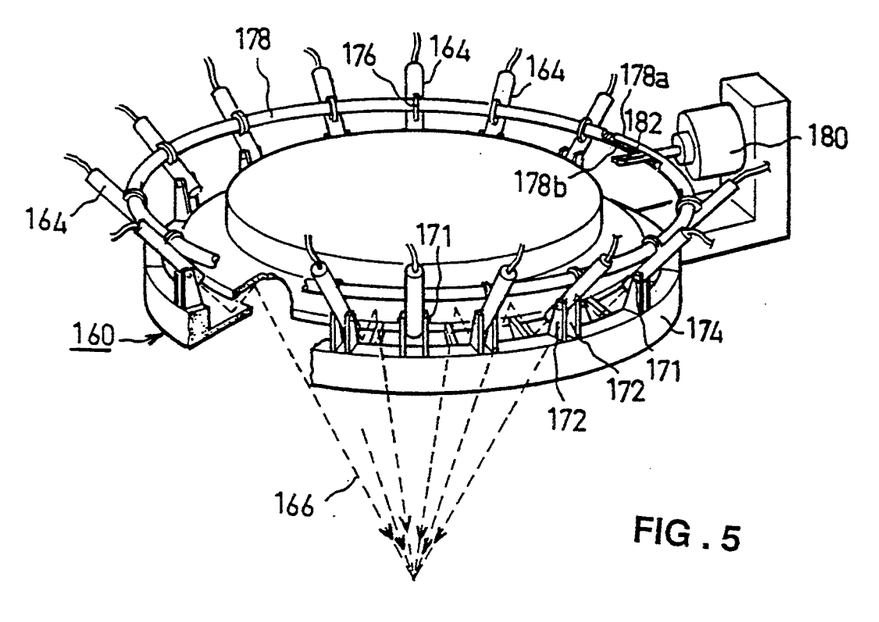
FIG. 5 is a perspective view illustrating an annular illuminator used in the apparatus of FIG. 4 for illuminating the interior of the eye being examined or treated.
Figure 6:
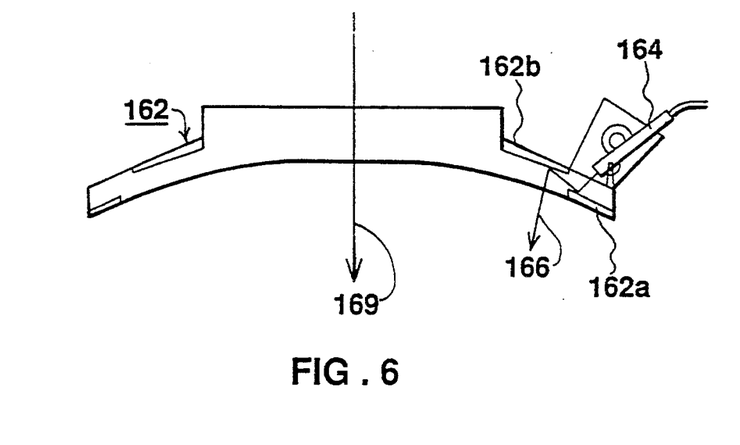
FIG. 6 is a side elevational view illustrating the annular illuminator of FIG. 5.

When using the apparatus illustrated in FIG. 3, the annular illuminator 160 illustrated in FIGS. 5–7 is placed over and in direct contact with the eye. The variable-diameter ring 178 is then adjusted by rotating knob 180 to pivot all the point light sources 164 such as to illuminate the region of interest of the eye, as illustrated in FIG. 4. The endoscope 150 (FIG. 3) is then inserted into the eye in alignment with the region of interest. While the interior of the eye is illuminated by the annular illuminator 160, the region of interest may be viewed via the endoscope 150, relay lens system 120, magnifier assembly 122, beam-folding prism 124, image intensifier 126, and the eyepiece 132 (or video camera if used), in the same manner as described above with respect to FIGS. 1 and 2. The area of interest in the eye may also be viewed directly, or by a microscope, through the central window 168 in the annular illuminator 160. If the interior of the eye is also to be treated by a laser beam, the laser is energized and its beam is directed by beam splitter 140 via the endoscope 150 into the eye, in substantially the same manner as described above with respect to FIGS. 1 and 2, except in this case that the laser (not shown) is mounted to pass its beam through the endoscope 150 rather than through the contact lens 10.

FIG. 9 illustrates a variation wherein the coupling collar 30 in FIGS. 1 and 2 is used for coupling thereto both an eyepiece 200 and a video camera 202, e.g., a CCD camera, to enable the area of interest of the eye being inspected also to be viewed from a remote location and/or to be recorded. It will be appreciated that the video camera attachment illustrated in FIG. 9 could also be applied to the apparatus illustrated in FIG. 3.

FIG. 9 also illustrates another method of illumination using an external light source, in this case an optical fiber 204 leading to a light source 205. The optical system in this case includes a barrier filter 206, a condensing lens system 208, and an annular mask 209 having a circular array of openings 210, which produces an annular array of light beams. These light beams are reflected from a beam splitter 210 within the housing onto the eye being examined so as to enter the eye also obliquely from a plurality of sides, and thereby to intersect at the plane of interest within the eye, as described above with respect to the embodiments of FIGS. 1, 2 and 3–8.

In all other respects, the apparatus illustrated in FIG. 9 is similar to that described above particularly with respect to FIGS. 1 and 2.

What is claimed is:

1. Ophthalmologic apparatus, comprising: illuminating means for directing light into an eye to be examined to illuminate a region of interest therein; a lens system for viewing said region of interest of the eye to be examined; an optical magnifier assembly for magnifying the viewed region of interest; and an image intensifier for intensifying the image of the viewed region of interest; wherein said illuminating means comprises: an annular light source; and an annular reflector coaxial with said annular light source for reflecting the light into the eye from all sides thereof to intersect in the plane of the region of interest in the eye.

2. The apparatus according to claim 1, wherein said illuminating means comprises means for changing the axial distance between the annular light source and the annular reflector to change the plane of intersection of the light.

3. The apparatus according to claim 1, wherein said annular light source comprises an annular array of point light emitters, and means for changing the angle of said light emitters with respect to the axis of said annular array to change the plane of intersection of the light.

4. The apparatus according to claim 1, wherein said lens system includes a contact lens engageable with the eye.

5. The apparatus according to claim 1, wherein said lens system, optical magnifiyer assembly and image intensifier are included within a housing, and wherein said housing further includes an attachment for attaching a laser thereto, and directing means for directing a laser beam emitted from said laser to said viewed region of the eye.

6. The apparatus according to claim 1, wherein said lens system, optical magnifiyer assembly and image intensifier are included within a housing, and wherein said housing further includes an eyepiece for eye viewing the region of interest, and a video camera for camera viewing the region of interest.

7. Ophthalmologic apparatus, comprising: illuminating means for directing light into an eye to be examined to illuminate a region of interest therein; a lens system for viewing said region of interest of the eye to be examined; an optical magnifier assembly for magnifying the viewed region of interest; an image intensifier for intensifying the image of the viewed region of interest; and an endoscope adapted to penetrate the eye for viewing a selected region thereof.

8. Ophthalmologic apparatus, comprising: an annular light source; an annular reflector coaxial with said annular light source for reflecting the light into an eye from all sides thereof to intersect in the plane of a region of interest in the eye; a housing including a lens system for viewing said region of interest of the eye to be examined; and an optical magnifier assembly within said housing for magnifying the viewed region of interest.

9. The apparatus according to claim 8, Wherein said illuminating means comprises means for changing the axial distance between the annular light source and the annular reflector to change the plane of intersection of the light.

10. The apparatus according to claim 9, wherein said annular light source comprises an annular array of point light emitters, and means for changing the angle of said light emitters with respect to the axis of said annular array to change the plane of intersection of the light.

11. The apparatus according to claim 8, wherein said lens system includes a contact lens engageable with the eye.

12. The apparatus according to claim 8, wherein the apparatus includes an endoscope adapted to penetrate the eye for viewing a selected region thereof.

13. The apparatus according to claim 8, wherein said housing further includes an attachment for attaching a laser thereto, and directing means for directing a laser beam emitted from said laser to said viewed region of the eye.

14. The apparatus according to claim 8, wherein said housing further includes an eyepiece for eye viewing the region of interest, and a video camera for camera viewing the region of interest.

* * * * *